United States Patent [19]

Gatto

[11] Patent Number: 5,130,484
[45] Date of Patent: Jul. 14, 1992

[54] TERTIARY AMIDES

[75] Inventor: Vincent J. Gatto, Baton Rouge, La.

[73] Assignee: Ethyl Corporation, Richmond, Va.

[21] Appl. No.: 670,287

[22] Filed: Mar. 15, 1991

Related U.S. Application Data

[63] Continuation-in-part of Ser. No. 518,486, May 3, 1990, abandoned.

[51] Int. Cl.$^5$ .............................. C07C 233/00
[52] U.S. Cl. ................... 564/219; 564/182; 252/51.5 A; 252/403
[58] Field of Search .......... 564/182, 223, 219; 252/403

[56] References Cited

U.S. PATENT DOCUMENTS

| | | | |
|---|---|---|---|
| 3,780,103 | 12/1973 | Knell | 564/219 |
| 3,927,091 | 12/1975 | Huber-Emden et al. | 252/402 |
| 3,996,194 | 12/1976 | Gencarelli et al. | 564/219 |
| 4,098,760 | 7/1978 | Cornell | 564/214 |
| 4,132,702 | 1/1979 | Schmidt et al. | 252/403 |

FOREIGN PATENT DOCUMENTS 7905000  3/1980 Netherlands .................. 564/219

OTHER PUBLICATIONS

Nikiforov et al., *Izvestiya Akademii Nauk SSSR, Seriya Khimicheskaya*, No. 12, pp. 2765-2770 (1989).

*Primary Examiner*—Allen J. Robinson
*Assistant Examiner*—Scott C. Rand
*Attorney, Agent, or Firm*—Patricia J. Hogan

[57] ABSTRACT

Tertiary amides having utility as antioxidants are compounds corresponding to the formula:

$$(p-HO-C_6R_nH_{4-n}-R''-CZZ')_2N-C(O)-R'$$

wherein R and R' are independently selected from alkyl, aryl, and benzyl groups, R'' is an alkylene group containing 1-4 carbons, Z and Z' are independently selected from hydrogen and alkyl, and n is an integer of 1-3.

11 Claims, No Drawings

TERTIARY AMIDES

CROSS-REFERENCE TO RELATED APPLICATION

This application is a continuation-in-part of copending application Ser. No. 518,486, filed May 3, 1990 now abandoned.

FIELD OF THE INVENTION

The invention relates to tertiary amides which are useful as antioxidants.

BACKGROUND

As disclosed in U.S. Pat. Nos. 3,780,103 (Knell), 3,927,091 (Huber-Emden et al.), 3,996,194 (Gencarelli et al.), 4,098,760 (Cornell), and 4,132,702 (Schmidt et al.) and Netherlands Patent Application 7905000 (Cincinnati Milacron Chemicals), it is known that some amides containing substituted hydroxyphenyl groups have been found to be useful as stabilizers for organic materials which are normally susceptible to oxidative deterioration.

N,N-bis(3,5-di-t-butyl-4-hydroxybenzyl)acetamide is disclosed by G. A. Nikiforov et al. in *Izvestiva Akademii Nauk SSSR, Seriva Khimicheskava*, No. 12, pp. 2765-2770, 1989.

SUMMARY OF INVENTION

The present invention resides in novel tertiary amides having advantages over known amides as antioxidants. These novel tertiary amides are compounds corresponding to the formula:

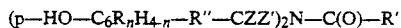
(p—HO—C$_6$R$_n$H$_{4-n}$—R''—CZZ')$_2$N—C(O)—R' wherein R and R' are independently selected from alkyl, aryl, and benzyl groups, R'' is an alkylene group containing 1-4 carbons, Z and Z'are independently selected from hydrogen and alkyl, and n is an integer of 1-3.

DETAILED DESCRIPTION

The novel tertiary amides of the invention are N,N-disubstituted carboxamides in which the chain length of the alkyl substituent para to the hydroxy group in each of the N-substituents is sufficient to separate the benzene ring from the amido group by at least two carbons. This is an important feature of the compounds, since it makes them superior to comparable compounds, such as the aforementioned N,N-bis(3,5-di-t-butylbenzyl)acetamide of Nikiforov et al., as antioxidants.

Although, as indicated by the formula, the p-alkyl substituent may have a branched chain when R'' is a branched alkylene group and/or at least one of Z and Z'is alkyl (usually an alkyl of only 1-4 carbons), it is apt to be most preferred for the R'' alkylene group to be unbranched and for Z and Z'to be hydrogen so that the R''—CZZ'of the formula is a -(CH$_2$)$_m$- group in which m is an integer of 2-5.

As also indicated by the formula, the novel tertiary amides may be derivatives of aliphatic or aromatic carboxamides, although it is generally preferred that they be derivatives of aliphatic carboxamides, i.e., compounds in which R' of the formula is an alkyl group, most preferably an alkyl group of 1-20 carbons. Also, although the R substituents on the p-hydroxyphenylalkyl groups may be 1-3 in number; may be alkyl, aryl, or benzyl; and, when there is more than one, may be the same or different, it is usually preferred that there be two substituents, which are most commonly alkyl groups containing 1-6 carbons (preferably 1-4 carbons), in the positions ortho to the hydroxy group.

Exemplary of the novel tertiary amides are the acetamides, propionamides, isopropionamides, butyramides, palmitamides, stearamides, and benzamides in which the N-substituents are β-(3,5-di-t-butyl-4-hydroxyphenyl)ethyl,β-(3-methyl-5-t-butyl-4-hydroxyphenyl)-ethyl, β-(3,5-diphenyl-4-hydroxyphenyl)ethyl, β-(3-benzyl-5-methyl-4-hydroxyphenyl)ethyl, β-(3-t-butyl-4-hydroxyphenyl)ethyl, β-(2-methyl3,5-di-t-butyl-4-hydroxyphenyl)ethyl, β-(3,5-diisopropyl-4-hydroxy phenyl)ethyl, γ-(3,5-di-t-butyl-4-hydroxyphenyl)propyl, γ-(3-methyl- 5-t-butyl-4-hydroxyphenyl)propyl, ⊖-methyl-γ-(3,5-di-t-butyl-4hydroxyphenyl)propyl, ε-(3-t-butyl-4-hydroxyphenyl)pentyl, or the like.

The preferred tertiary amides of the invention are N,N-bis[β-(3,5-di-t-butyl-4-hydroxyphenyl)ethyl]acetamide, N,N-bis[β(3,5-di-t-butyl-4-hydroxyphenyl)ethyl]stearamide, N,N-bis[β-(3,5-diisopropyl-4-hydroxyphenyl)ethyl]acetamide, and N,N-bis-[β-(3-methyl-5-t-butyl-4-hydroxyphenyl)ethyl]acetamide. Of these amides, the one that is most preferred is N,N-bis[β-(3,5-di-t-butyl-4-hydroxyphenyl)ethyl]acetamide.

The tertiary amides may be prepared by reacting the appropriate acyl halide corresponding to the formula R'COX with the appropriate secondary amine corresponding to the formula:

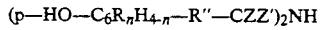
(p—HO—C$_6$R$_n$H$_{4-n}$—R''—CZZ')$_2$NH

X representing halo, preferably chloro or bromo; and R, R', R'', Z, Z', and n being as previously defined. Thus, for example, an acyl halide such as acetyl chloride, propionyl chloride, butyryl bromide, isobutyryl chloride, stearoyl chloride, or benzoyl chloride is reacted with a secondary amine such as bis[β-(3,5-di-t-butyl-4hydroxyphenyl)ethyl]amine, bis[γ-(3-methyl-5-t-butyl-4-hydroxyphenyl)propyl]amine, or other such amine.

In the synthesis of the tertiary amides, the amines and acyl halides are reacted in a mol ratio of about 0.5-1/1, preferably about 0.9/1, in a solvent which is inert to the reaction and which is capable of solubilizing both the reactants and the product and optionally in the presence of an acid scavenger which can neutralize acid produced by the reaction without adversely affecting the process.

Solvents suitable for use in the reaction include, e.g., toluene, benzene, xylene, mesitylene, chlorobenzene, methylene chloride, chloroform, carbon tetrachloride, 1,2-dichloroethane, 1,1,2-trichloroethane, and the like, the preferred solvents usually being toluene and methylene chloride.

Examples of acid scavengers which may be used in the process are triethylamine, tripropylamine, tributylamine, pyridine, and the like, with the preferred acid scavenger being triethylamine. When employed, the acid scavenger is used in an amount such as to provide about one mol of acid scavenger per mol of acid generated by the reaction.

In the preparation of the tertiary amides, the components of the reaction mixture are combined in any suitable way, conveniently by adding a solution of the amine (and optionally also an acid scavenger) in a portion of the solvent to a solution of the acyl halide in the remainder of the solvent over a period of about 0.5-1 hour while maintaining the reaction mixture at a temperature of about 0°-25° C. Then, when combination of the reactants is at least substantially complete, the temperature is raised, if necessary, to be in the range of about 10°-45° C., preferably about 25°-35° C., and kept in that range for about 2-10 hours. It is ordinarily most convenient in this reaction to use ambient temperature.

After completion of the reaction, the product can be recovered in any suitable way. For example, the reaction mixture may be diluted with solvent, preferably the same solvent as was used in the reaction; the diluted reaction mixture may then be washed with an inorganic acid, such as HCl; the organic phase resulting from this wash may be recovered and washed with a base, such as NaOH; the organic phase resulting from this wash may be recovered and washed with a salt solution, e.g., aqueous NaCl; and the organic phase resulting from this wash may be recovered and dried to yield the desired tertiary amide.

The tertiary amides of the invention are especially useful as antioxidants for organic materials which are normally susceptible to oxidative deterioration, such as the organic materials taught in Knell, Huber-Emden et al., Gencarelli et al., and Schmidt et al., the teachings of all of which are incorporated herein by reference. They are particularly useful in this regard when used to stabilize olefin polymers and copolymers, e.g., polyethylene, polypropylene, etc.

When used as antioxidants, the tertiary amides may be employed as the sole stabilizers for the normally-oxidizable organic materials, or they may be used in conjunction with other stabilizers, such as conventional phenolic antioxidants, thioester synergists, etc. Moreover, their activity as antioxidants does not appear to be inhibited by the presence in the organic materials of additives such as those conventionally employed in such materials, e.g., light stabilizers, ultraviolvet light absorbers, metal deactivators, pigments, dyes, lubricants, nucleating agents, fillers, and the like.

As already mentioned, the tertiary amides of the invention have an advantage over comparable amides, such as the N,N-bis(3, 5-di-t-butylbenzyl)acetamide of Nikiforov et al., in this application because of their having at least two carbons between each benzene ring and the amido nitrogen. This feature of their structure provides better long-term stability to the compositions in which they are used, thus making them valuable for protecting the organic materials both during processing and later.

The following examples are given to illustrate the invention and are not intended as a limitation thereof. Unless otherwise specified, quantities mentioned in the examples are quantities by weight.

EXAMPLE I

Charge a suitable reaction vessel with 1.6g of acetyl chloride and 10 mL of dry toluene. While stirring the reaction mixture and maintaining the temperature at 0°-8° C., slowly add a solution of 9g of bis[β-(3,5-di-t-butyl-4-hydroxyphenyl)ethyl]amine, 2.1g of triethylamine, and 30 mL of dry toluene. Then allow the reaction mixture to reach ambient, i.e., room, temperature, and maintain that temperature for four hours.

After completion of the four-hour period, wash the reaction mixture consecutively with 50 mL of 3N HCl, 50 mL of 1N NaOH, and 50 mL of a saturated aqueous NaCl solution, the organic phase being recovered after each wash and then subjected to the next wash. Recover the final washed organic phase, dry, and concentrate in vacuo to provide a 98% yield of N,N-bis[β-(3,5-di-t-butyl-4-hydroxyphenyl)ethyl]acetamide. Recrystallize the crude product from 100 mL of heptane and wash the precipitated product with 75 mL of heptane. GC analysis shows the recrystallized product to contain 99% of the tertiary amide, which has a melting point of 153°-155° C. Spectral analyses H-NMR, $^{13}$C-NMR, IR GC-MS) confirm the identity of the solid as N,N-bis[β-(3,5-di-t-butyl-4-hydroxyphenyl)ethyl]acetamide.

EXAMPLE II

Subject the product of Example I to thermogravimetric analysis by heating different samples of the product at 10° C./minute from 25° C. under nitrogen and air, respectively. The results of the analysis are shown below.

| % Weight Loss | Temperature (°C.) | |
|---|---|---|
| | Under Nitrogen | Under Air |
| 10 | 298 | 282 |
| 50 | 339 | 320 |
| 90 | 360 | 343 |

As shown by this analysis, the product has low volatility and hence good thermal stability.

EXAMPLE III (COMPARATIVE)

Repeat Example II except for performing the analysis on N,N-bis(3,5-di-t-butyl-4-hydroxybenzyl)acetamide instead of the product of Example I. The results of the analysis are shown below.

| % Weight Loss | Temperature (°C.) | |
|---|---|---|
| | Under Nitrogen | Under Air |
| 10 | 245 | 249 |
| 50 | 281 | 286 |
| 90 | 330 | 307 |

As shown by the results of the analysis, this product, in which there is only one carbon between the amido group and each of the benzene rings, is more volatile and thus has poorer thermal stability than the product of Example I.

EXAMPLE IV

Part A

Prepare three blends of polypropylene powder, 0.05% of calcium stearate as a lubricant, and 0.1% of:

| Blend | Antioxidant |
|---|---|
| A | N,N-bis[β-(3,5-di-t-butyl-4-hydroxyphenyl)ethyl]acetamide |
| B | N,N-bis(3,5-di-t-butyl-4-hydroxybenzyl)acetamide |
| C | N,N-bis[β-(3,5-di-t-butyl-4-hydroxyphenyl)ethyl]-2,2,2-trichloracetamide |

Part B

Test the compositions of Part A for melt flow index and yellowness index by extruding them in a Brabender twin screw extruder at 150°-245°-245° C. and 30 rpm under nitrogen and then making five passes through a Brabender single screw extruder at 260°-260°-26-

0°–260° C. and 30 rpm with ambient air. The test results are shown below.

| Blend | MFI @ 230° C./2160 g Load Extrusion Passes | | | | Yellowness Index Extrusion Passes | | |
|---|---|---|---|---|---|---|---|
| | TwS | ss1 | ss3 | ss5 | ss1 | ss3 | ss5 |
| A | 5.2 | 6.5 | 9.0 | 13.2 | 5.0 | 6.4 | 7.9 |
| B | 4.7 | 5.2 | 6.5 | 9.0 | 5.3 | 6.7 | 9.3 |
| C | 4.7 | 5.0 | 6.3 | 7.4 | 6.2 | 10.0 | 15.0 |

Part C

Test the compositions of Part A for resistance to failure on oven aging by (1) molding pellets of the compositions retained from the twin screw pass of Part B into plaques having a thickness of ~0.06 cm, using a hydraulic press set at 245° C. for the molding, (2) cutting each of the plaques into five ~2.5 cm squares, (3) placing each of the squares into glass Petri dishes, (4) placing the Petri dishes into an air-circulating oven set at 150° C., and (5) checking the samples every 24 hours for failure—failure being determined when at least three of the five squares of a particular composition are visually decomposed. The test results are shown below.

| Blend | Total Hours @ Failure |
|---|---|
| A | 96 |
| B | 48 |
| C | 120 |

These test results show that (1) the antioxidant of Blend B, i.e., the compound of Nikiforov et al., contributes more color and much poorer resistance to oven aging and (2) the antioxidant of Blend C, i.e., a compound taught by Cornell, gives much poorer color than an antioxidant of the present invention.

What is claimed is:

1. A tertiary amide corresponding to the formula:

$$(p\text{—}HO\text{—}C_6R_nH_{4-n}\text{—}R''\text{—}CZZ')_2N\text{—}C(O)\text{—}R'$$

wherein R and R' are independently selected from alkyl, aryl, and benzyl groups, R" is an alkylene group containing 1–4 carbons, Z and Z' are independently selected from hydrogen and alkyl, and n is an integer of 1–3.

2. The tertiary amide of claim 1 wherein R is an alkyl group of 1–6 carbons.

3. The tertiary amide of claim 2 wherein R is an alkyl group of 1–4 carbons.

4. The tertiary amide of claim 3 wherein R is t-butyl.

5. The tertiary amide of claim 1 wherein n is 2.

6. The tertiary amide of claim 1 wherein R"—CZZ' is $(CH_2)_m$ in which m is an integer of 2–5.

7. The tertiary amide of claim 1 wherein R' is an alkyl group of 1–20 carbons.

8. The tertiary amide of claim 7 wherein R' is methyl.

9. The tertiary amide of claim 7 wherein R' is heptadecyl.

10. The tertiary amide of claim 1 wherein R is an alkyl group of 1–4 carbons, n is 2, R"—CZZ' is $(CH_2)_m$ in which m is an integer of 2–5, and R' is an alkyl group of 1–20 carbons.

11. The tertiary amide of claim 10 which is N,N-bis[β-(3,5-di-t-butyl-4-hydroxyphenyl)ethyl]acetamide.

* * * * *